(12) United States Patent
Murphy

(10) Patent No.: US 6,409,756 B1
(45) Date of Patent: Jun. 25, 2002

(54) ENDOVASCULAR AORTIC GRAFT

(76) Inventor: Edward G. Murphy, 6035 E. Sage Dr., Scottsdale, AR (US) 85253

( * ) Notice: Subject to any disclaimer, the term of this patent is extended or adjusted under 35 U.S.C. 154(b) by 0 days.

(21) Appl. No.: 09/489,401

(22) Filed: Jan. 24, 2000

(51) Int. Cl.⁷ .................................................. A61F 2/06
(52) U.S. Cl. ..................................... 623/1.35; 623/1.16
(58) Field of Search .......................... 606/198, 195; 623/1.13–1.15, 1.35

(56) References Cited

U.S. PATENT DOCUMENTS

| | | | | |
|---|---|---|---|---|
| 5,609,627 A | * | 3/1997 | Goicoechea et al. | 623/1 |
| 5,667,523 A | * | 9/1997 | Bynon et al. | 606/198 |
| 5,693,087 A | * | 12/1997 | Parodi | 623/1 |
| 5,720,776 A | | 2/1998 | Chuter et al. | 623/1 |
| 5,755,770 A | | 5/1998 | Ravenscroft | 623/1 |
| 5,800,518 A | | 9/1998 | Piplani et al. | 623/1 |
| 6,102,940 A | * | 8/2000 | Robichon et al. | 623/1 |
| 6,152,956 A | * | 11/2000 | Pierce | 623/1.13 |
| 6,162,246 A | * | 12/2000 | Barone | 623/1.35 |
| 6,168,619 B1 | * | 1/2001 | Dinh et al. | 623/1.13 |

* cited by examiner

*Primary Examiner*—Corrine McDermott
*Assistant Examiner*—Hieu Phan

(57) ABSTRACT

An arterial interluminal prosthesis for repairing an aortic aneurysm of a patient comprising. The prosthesis includes a main body having an upper end with a upper aperture for being located proximate to renal arteries of the patient and a lower end having two lower apertures for being located in the arortic artery proximate iliac arteries of the patient. The prosthesis also includes a first leg that is separate from the main body that is inserted into one of the two lower apertures of the main body to extend therefrom into one of the iliac arteries and a second leg separate from the main body that is inserted into the other of the two lower apertures of the main body to extend therefrom into the other of the iliac arteries.

17 Claims, 2 Drawing Sheets

ENDOVASCULAR AORTIC GRAFT

FIELD OF INVENTION

This invention relates generally to an interluminal prosthesis for the repair of body conduits. More particularly, the invention relates to an interluminal device for insertion into a body conduit for repair of damaged portions thereof.

BACKGROUND OF THE INVENTION

The present invention is particularly useful for the repair of an aortic aneurysm. Aortic aneurysms are an abnormal dilation of the aorta that if not repaired can burst and kill the patient. Interluminal devices for repairing these aneurysms are known in the art. The devices are typically comprised of flexible grafts that are inserted into the aorta via open surgery.

The surgical procedures for repairing aneurysms are major undertakings that replace a portion of the aorta with a prosthetic device. Generally, these prosthetic devices are comprised of a synthetic tube or graft, typically formed of Dacron, Teflon or other suitable material. In particular procedures, the aorta is clamped above and below the aneurysm cutting off the normal flow of blood through the aorta. The aneurysm portion of the aorta is removed and a graft having a diameter approximately the same size as the normal diameter of the aorta is sutured to the two cut ends of the aorta to structurally replace the aneurysm. Generally, this is a very difficult procedure for the patient and requires extensive recovery time. Also, the incision extends from the xiphoid to the pubic bone and accompanies a significant amount of complication. Thus, the patient has a significant incision extending down the abdomen and must recover from this intrusive procedure.

In order to overcome the difficulties with these surgeries, several procedures have been suggested for the insertion of a raft through the femoral and iliac arteries. These procedures involve the compression of the graft so that it can be inserted through the femoral artery, up the iliac artery and then, when it is positioned in the aorta across the aneurysm, the graft is expanded with stents. This interluminary insertion of the graft can result in a significant reduction in the trauma and complication of the surgery.

The prosthetic devices used in these procedures are comprised of a generally tubular graft for insertion into the aorta with two integral legs extending therefrom for extending from the aorta into the iliac arteries.

U.S. Pat. No. 5,720,776, for example, discloses a prosthesis assembly for placement at an aneurism in the bifurcated lumen of the aorta and the iliac arteries extending therefrom. The prosthesis assembly includes a single lumen graft or a bifurcated lumen graft having a main body and ipsilateral and contralateral limbs extending therefrom. The main body and ipsilateral and contralateral limbs each have a spring assembly around their orifices for conforming that portion of the graft to the wall of the vessel lumen. The main body spring includes a barb with first and second arms for securely anchoring the spring assembly to the vessel wall. The ipsilateral and contralateral spring assemblies also include the barb with only a single attachment arm for anchoring the spring assembly to the vessel wall.

Similarly, U.S. Pat. No. 5,755,770 discloses an arterial interluminal prosthesis for repairing aneurysm and connecting to iliac arteries. The prosthesis includes a generally tubular, flexible graft with a proximate end and two distal ends. Each of the distal ends includes integral legs which bifurcate from the graft. The prosthesis includes a first stent disposed within and emerging from the proximate end and is adapted to attach to the aorta. A hem terminating in the distal end of the graft is inverted within the leg. A second stent having a proximal end and distal end can be attached to the interior of the distal end of the cuff so that upon withdrawing the second stent from the cuff, the cuff will unfold and follow the stent for implantation of the graft.

U.S. Pat. No. 5,800,518 also discloses a graft having a bifurcation for repairing a aortic aneurism. The graft includes a main tubular body and integrally formed first and second tubular legs. The first leg has an opening associated therewith and the second tubular leg includes an lead tube attached to the proximate end. For implementation, the second leg is folded over so that it is oriented in the same direction as the main opening. Then the graft is inserted using a lead tube through the first iliac artery. After the main body is secured to the aortic artery the second leg is pulled into the second iliac artery by pulling on the lead tube.

However, the grafts disclosed in each of these references have shortcomings that make the insertion procedure difficult and time consuming. The present invention is directed to a graft that is significantly easier to insert. None of the references disclose a arterial interluminal graft or method of inserting an arterial interluminal graft according to the present invention as set forth in detail below.

SUMMARY OF THE INVENTION

The present invention is directed towards an arterial interluminal prosthesis for repairing an aortic aneurysm of a patient. The aterial interluminal prosthesis includes a main body having a first end with a first aperture that, when inserted into the aortic artery, is located proximate to the renal arteries of the patient. The main body also includes a second end having at least one lower aperture located within the aortic artery and above the entrance to one of the iliac arteries. Preferably, the invention includes two lower apertures that are located in the aortic artery and proximate to the entrances of the iliac arteries of the patient. The invention is also directed to a first leg that is separate from the main body such that it can be inserted into one of the two lower apertures of the main body to extend therefrom into one of the iliac arteries. Further, the invention preferably includes a second leg that is also separate from the main body such that it can be inserted into the other of the two lower apertures of the main body to extend therefrom into the other of the iliac arteries.

In one particular embodiment, the present invention is directed to an arterial interluminal prosthesis further comprising a first stent located entirely within the main body proximate the first end and a second stent coupled at the first end of the main body such that it extends from the main body and across the renal arteries of the patient. Preferably, the second stent is coupled to the first stent and an upper edge of the main body such that it has a restricted lower end and is unrestricted at the opposing, upper end such that the upper end can expand to hold the prosthesis in place.

The present invention is also directed to an arterial interluminal prosthesis having a main body with first and second ends. The main body has a first stent coupled to the inside of the main body proximate the first end and at least one outer stent coupled to the outside surface of the main body below the first stent and proximate to the lower end of the main body. Preferably, the outer stent is coupled to the lower end of the first stent through the wall of the main body.

Preferably, the first, second and outer stents are Z stents. Most preferably, the first, second and outer Z stents are between about 15 and 40 mm, depending on the diameter of the patient's aorta.

The present invention also includes an embodiment where the arterial interluminal prosthesis has a main body and separate legs further comprised of wall stents in each of the first leg and the second leg. Preferably, the wall stents are substantially the same length as the corresponding legs. More preferably, the wall stents are longer than the corresponding legs such that they extend therefrom to attach to the iliac artery and the main body.

In a preferred embodiment of the present invention, the main body further includes two extensions at the second end for extending towards the iliac arteries. The two extensions have first diameters and the first and second legs have second diameters that are larger than the first diameters to substantially seal the extensions and the main body such that the patients blood flows through the main body and leg members. Preferably, the two extensions further include Z-stents coupled to the outer surface of the extensions and leg members abut the inner surface of the extensions to seal the same.

The present invention is also directed to a method of inserting an arterial interluminal prosthesis into an aortic artery and iliac artery of a patient. The method includes the steps of providing a main body having a first end with an upper aperture and second end having at least one lower aperture and inserting the main body through a first iliac artery into the aortic artery such that the first end is located proximate to the renal arteries of the patient and the second end is located in the aortic artery, proximate the iliac arteries of the patient. Then a first leg member that is separate from the main body is inserted through the first iliac artery and into the at least one lower aperture of the second end of the main body to extend therefrom into the first iliac artery. If two legs are to be used, a second leg that is also separate from the main body is inserted through a second iliac artery and into a second lower aperture of the second end of the main body to extend therefrom into the second iliac artery.

In one embodiment of the invention, the method of inserting an arterial interluminal prosthesis into an aortic artery and iliac arteries of a patient also includes the steps of coupling a first stent to the upper edge of the first aperture of the main body and inserting the first stent into the aortic artery through a first sheath such that the first stent extends across the renal arteries and secures the main body in the aortic artery. Also, the method can include providing wall stents in first and second leg grafts that are longer than the first and second leg grafts and inserting the first and second legs though a second sheath that has a smaller diameter than the first sheath such that the wall stents extend into the main body beyond first ends of the first and second leg grafts such that the wall stents hold the first and second leg grafts to the main body. When the leg members are inserted into the extensions of the main body, the wall stents are expanded such that they abut the inner walls of the main body. Preferably, the leg members are inserted into the main body to approximately the same level. Also, preferably, the wall stents extended beyond the second, lower ends of the first and second leg grafts such that the wall stents hold the first and second leg members to the first and second iliac arteries.

DETAILED DESCRIPTION OF THE INVENTION

Figure 1:
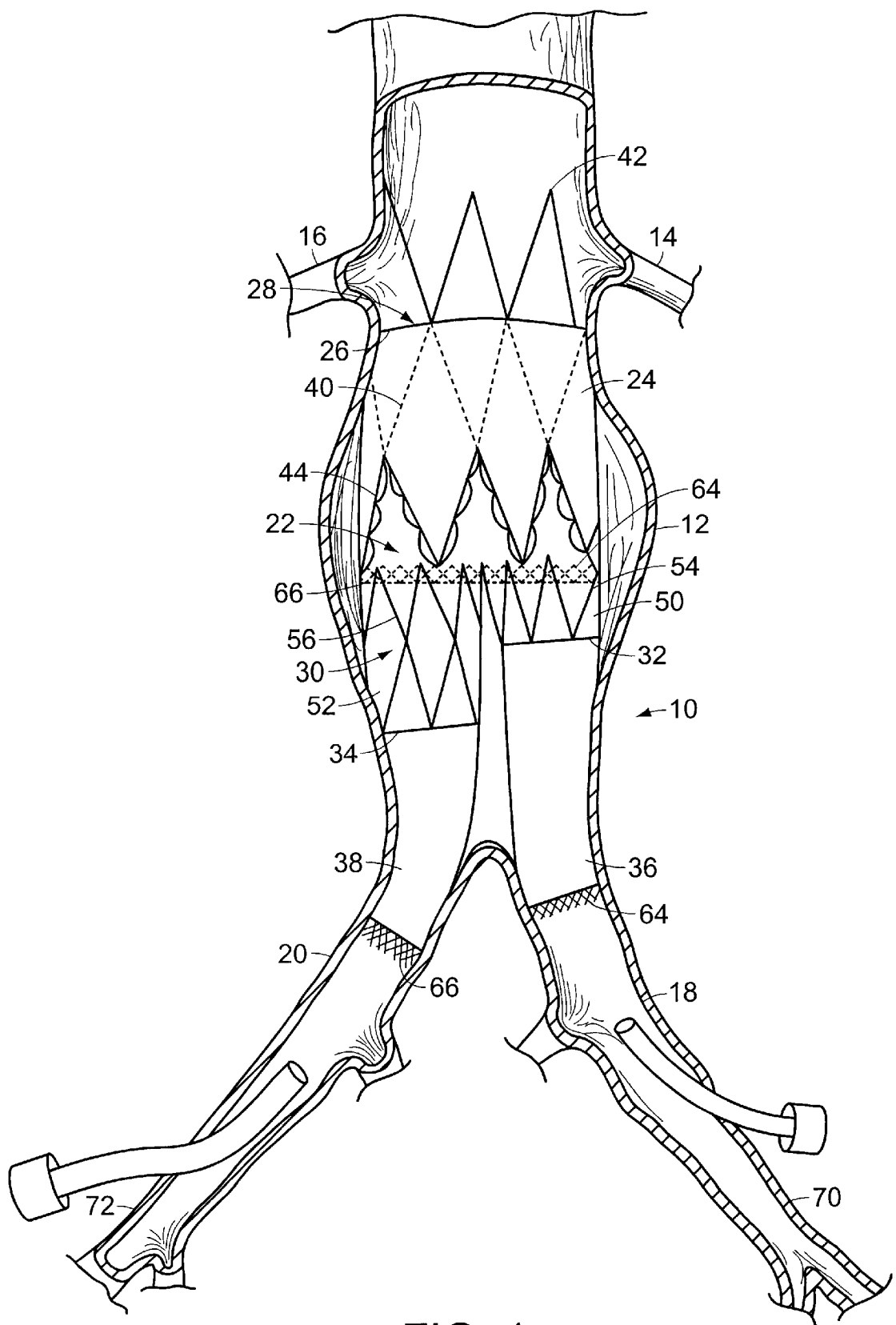
FIG. 1 is a plan view of a first embodiment of an arterial interluminal prosthesis according to the present invention positioned in the aortic artery.

The present invention is directed towards an arterial interluminal prosthesis or aortic endograft for repairing an aortic aneurysm of a patient. In FIG. 1, the patient's aortic artery 10 includes and aneurysm 12, which is a large ballooning or increased diameter portion of the aortic artery 10. Aneurysms generally accure between the renal arteries 14 and 16 and the iliac arteries 18 and 20.

The aterial interluminal prosthesis or aortic endograft 22 includes a main body 24 having a first, upper end 26 with a first aperture 28 that, when inserted into the aortic artery, is located adjacent to and below the renal arteries 14 and 16 of the patient. The main body 24 also includes a second end 30 having at least one aperture 32 or 34 located in the aortic artery 10, proximate the entrance to one of the iliac arteries 18 or 20. Preferably, the invention includes two apertures 32 and 34 that are located in the aortic artery and proximate to the entrances of both of the iliac arteries of the patient 18 and 20. Generally, only one aperture 32 or 34 will be used in the instances when the patient has one iliac artery that is in very poor condition or is substantially twisted to the point that it is better to bypass the iliac artery and graft between the femoral arteries at a lower point in the body. In these instances, an inclusion graft (not shown) must be placed at the upper end of the poor conditioned iliac artery.

The aortic endograft 22 also includes at least a first leg member 36 that is separate from the main body 24, i.e., is not integrally formed with the main body 24 or permanently coupled to the main body 24. Thus, the leg member 36 can be inserted into one of the two apertures 32 of the main body 24 to extend therefrom into one of the iliac arteries 18. Further, the preferred embodiment includes a second leg member 38 that is also separate from the main body 24 such that it can be inserted into the other of the two apertures 34 of the main body 24 to extend therefrom into the other of the iliac arteries 20.

In the preferred embodiment, the aortic endograft 22 has a first stent 40 located entirely within the main body 24 such that the upper end of the stent is adjacent to the first end 26 and a second stent 42 is coupled at the edge of the aperture 28 of the main body 24 such that it extends from the main body 24. Both of these stents are preferably Z-stents having a diameter of about 15 to 40 mm, such that the stent is slightly larger that the aortic artery being grafted. When the aortic endograft 22 is located in the patient, the second stent 42 is located in the aortic artery 10 such that it extends across the orifices of the renal arteries 14 and 16 of the patient. Preferably, the second stent 42 is coupled to the top suture of the first stent 40 and an upper edge of the main body 24 with sutures such that it has a restricted diameter at the lower end and is unrestricted at the opposing, upper end such that the upper end can expand to the diameter of the aorta 10 and hold the endograft 22 in place.

In the preferred embodiment, the main body 24 has the first stent 40 coupled to the inside surface of the main body 24 proximate the first end 26 as set forth above and at least one lower stent 44 is coupled to the outside surface of the main body 24 proximate the second end 30 via sutures. Preferably, the upper end of the outer, lower stent 44 is also coupled to the first stent 40 through the wall of the main body using sutures. In this manner, the inside surface of the aorta 10 has minimal flow restrictions and the outer stent 44 can assist in keeping the endograft 22 in place. Furthermore, by coupling the outer, lower stent 44 to the first stent 40, the endograft's structural integrity is increased by providing stents that extend along substantially the entire length of the endograft. Sutures also couple the wall of the graft to a plurality of locations along each strut of the stent, such that the diameter of the endograft 24 is maintained.

Extending from the main body 24 are two extensions 50 and 52. The extensions 50 and 52 are relatively short, i.e., less than about ⅓ the length of the main body 24, and extend toward the openings of the iliac arteries 18 and 20. Each of the extensions preferably has a diameter about the same as the opening to the iliac arteries and included Z-stents 54 and 56 coupled to the inner surface of the extensions. Also, the extension Z-stents 54 and 56 can be coupled to the outer, lower Z-stent 44.

Figure 2:
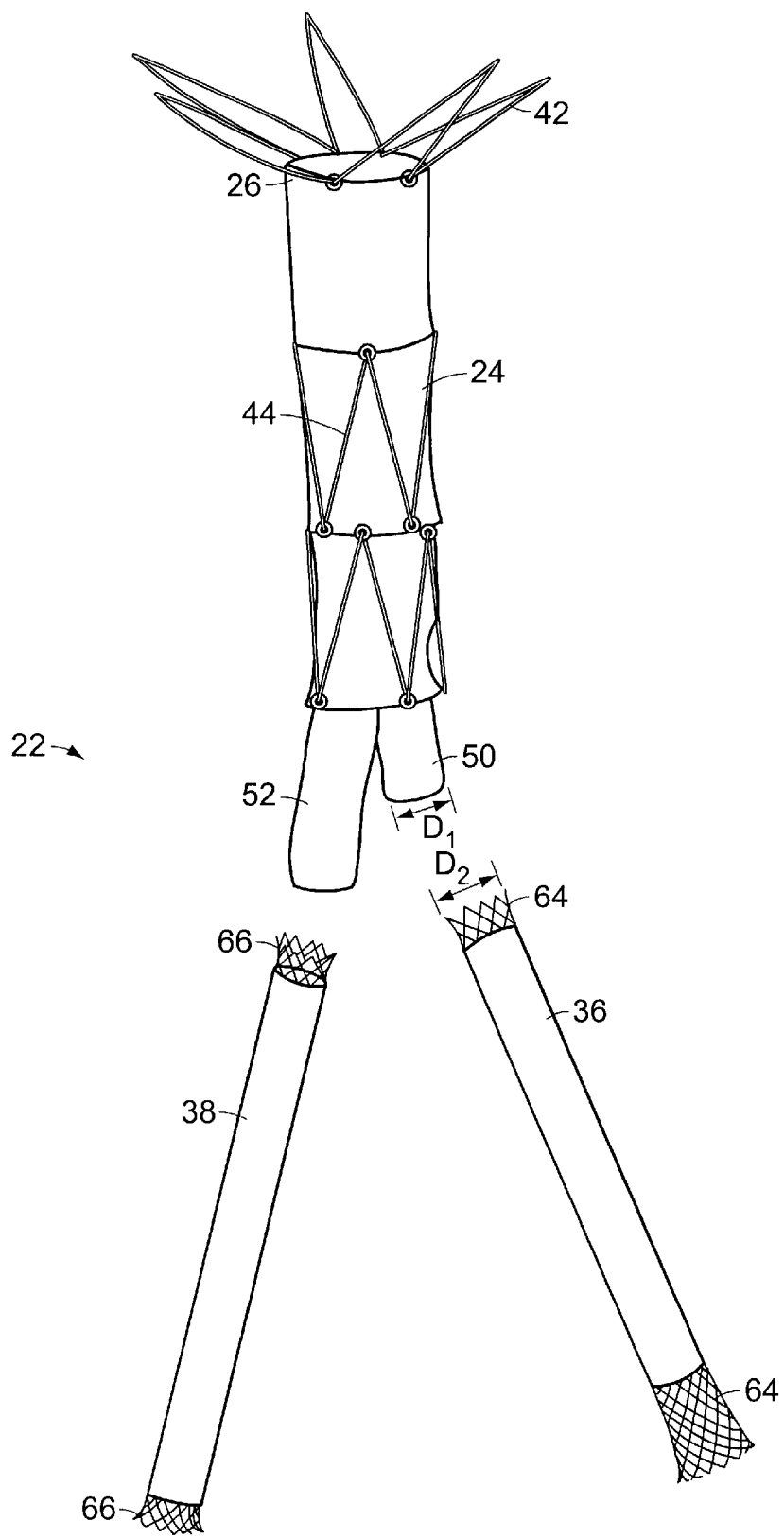
FIG. 2 is a plan view of a second emodiment of an arterial interluminal prosthesis according to the present invention.

Referring to FIGS. 1 and 2, the endograft 22 also includes separate legs 36 and 38 that extend from the main body extensions 50 and 52 respectively and into the iliac arteries 18 and 20. The leg members are separate members from the main body 24 in that they are not formed integrally with the main body 24 or permanently coupled to the main body 24. Because of this, the main body 24 can be inserted into the aortic artery 10 through a first iliac artery 18 such that the first extension 50 is oriented toward the opening of the iliac artery 18, as explained in more detail below. Then using a smaller catheter, the first leg member 36 can be inserted into the first iliac artery 18 and the first extension 50 of the main body 24. Once this has been inserted, the second leg member 38 can be inserted into the second iliac artery 20 and into the second extension 52 of the main body 24.

The separate leg members 36 and 38 preferably have wall stents 64 and 66 located within the leg members 36 and 38. Even more preferably, the wall stents 64 and 66 are substantially the same length as the corresponding leg members 36 and 38. The wall stents 64 and 66 are most preferably slightly longer than the corresponding leg members 36 and 38. As shown, the wall stents 64 and 66 extend from both ends of the leg members 36 and 38. In this manner, the wall stents 64 and 66 can couple the leg members 36 and 38 to the main body 24 once they have been inserted into the iliac arteries. Also, the lower ends of the wall stents 64 and 66 preferably extend beyond the lower ends of the leg members 36 and 38 and abut the iliac arteries to hold leg members in place. The two extensions 50 and 52 also have first diameters and the first and second leg members 36 and 38 have second diameters that are larger than the first diameters to seal the lower end of the extensions 50 and 52 and the main body 24 such that the patients blood flows through the main body 24 and through the leg members 36 and 38.

The present invention is also directed to a method of inserting an arterial interluminal prosthesis into an aortic artery and iliac artery of a patient. The method generally includes the steps of providing a main body 24 having a first end 26 with a first aperture 28 and second end 30 having at least one aperture 32 and 34 and inserting the main body 24 through a first iliac artery 18 or 20 into the aortic artery 10 such that the first end 26 is located proximate to the renal arteries 14 and 16 of the patient and the second end 30 is located in the arotic artery 10, proximate to the openings of the iliac arteries 18 and 20 of the patient. Then a first leg member 36 that is separate from the main body 24 is inserted through the first iliac artery 18 and into the first aperture 32 of the second end of the main body to extend therefrom into the first iliac artery 18. In most instances, where two legs are to be used, a second leg member 38 that is also separate from the main body 24 is inserted through a second iliac artery 20 and into the second aperture 34 of the second end of the main body to extend therefrom into the second iliac artery 20.

More particularly, the patient is placed under general or spinal anesthesia. Two small groin incisions are made to expose the femoral arteries 70 and 72. With the femoral arteries exposed in the groin, the patient is anticoagulated with Heparin and the femoral arteries are clamped distally to prevent embolization down the legs. The straightest femoral artery is punctured with an angiographic needle, a wire guide is passed through the needle up the iliac artery and through the aneurysm. Then a femoral sheath, which is a small plastic tube that holds open the puncture site allowing the exchange of catheters and wires as needed, is positioned into the femora artery.

An angiographic catherter is passed over the guide wire up to the renal arteries. The wire is then removed and an aortic angiogram is performed to locat the level of the renal arteries and outline the neck of the aneurysm. After this has been localized and marked, the wire is reinserted through the catheter. The catheter and sheath are removed and a large sheath, 16–20 F, is inserted up the first iliac artery, through the aneurysm, and positioned just above the renal arteries.

The main body of the endograft, having a diameter approximate the neck of the aneurysm is put into a loading sheath, which is generally one size smaller than the large sheath. Using a push rod, the main body is pushed from the loading sheath into the large sheath and up to above the renal arteries. Holding the push rod in a steady position, the large sheath is pulled back over the push rod, allowing the main body to expand into the aortic artery. In this manner, the upper stent that extends from the upper end of the main body lies across the opening of the renal arteries and the upper end of the main body is located below and adjacent to the renal arteries.

Once the main body of the endograft has been deployed in the aorta, the other femoral artery is punctured and an angled wire is passed up the second ilia artery. A smaller sheath is then placed in the femeral puncture along the wire. Using the angled wire and a small angled catheter, the second limb of the main body is canulated. Thus, there is a guide wire extending into each extension of the main body. Small sheaths, 12–16 F, are then fed along the wires into the extensions of the main body.

A first leg member, comprised of a graft with internal wall stent, is fed through the first small sheath and positioned such that the upper end therof is located within the main body. Then the first small sheath is pulled back to allow the first leg member to expand into the main body and into the first iliac artery. Then this is repeated on the second side to insert the second leg member.

Following the positioning of the two leg members, a catheter is then passed up to the renal arteries. An aortic angiogram is then preformed to confirm that the endograft does not have any leaks. Then the sheaths and wires are removed from the femoral arteries. The arteries are clamped at the proximal ends and flushed to make sure there is no loose debrit in the vascular system. The femoral arteries are then sutured and the clamps are removed. The groin incisions are then closed in standard practice.

As stated above, preferably the method includes providing wall stents in the first and second legs that are longer than the first and second and extending the wall stents into the main body beyond first ends of the first and second legs such that the wall stents are positioned in the extension members to hold the first and second legs to the main body. The wall stents also extended beyond the second ends of the first and second leg members such that the wall stents hold the first and second legs to the first and second iliac arteries.

While it is apparent that the illustrative embodiments of the invention herein discloses fulfills the objective stated above, it will be appreciated that numerous modifications and other embodiments may be devised by those skilled in the art. Therefore, it will be understood that the appended claims are intended to cover all such modifications and embodiments which come within the spirit and scope of the present invention.

I claim:

1. An arterial interluminal prosthesis for repairing an aortic aneurysm of a patient comprising:
    a main body having a first end with an upper aperture for being located proximate to renal arteries of the patient and a second end having two lower apertures for being located in the aortic artery proximate iliac arteries of the patient;
    a first leg separate from the main body for inserting into one of the two lower apertures of the main body to extend therefrom into one of the iliac arteries;
    a second leg separate from the main body for inserting into the other of the two lower apertures of the main body to extend therefrom into the other of the iliac arteries; and
    a first stent located entirely within the main body proximate the first end and a second stent coupled at the first end of the main body to extend therefrom across the renal arteries of the patient.

2. The arterial interluminal prosthesis of claim 1, further comprising at least one outer stent coupled to an outside surface of the main body proximate the second end of the main body such that the first sent supports a first portion of the main body exclusively from the inner surface of the main body and the outer stent supports a second portion of the main body exclusively from the outer surface of the main body.

3. By The arterial interluminal prosthesis of claim 2, wherein the outer stent is coupled to the first stent.

4. The arterial interluminal prosthesis of claim 2, comprising a plurality of stents coupled to the outer surface of the main body, wherein at least one of such stents is located proximate the second end of the main body and the at least one other of such stents is coupled to the first stent such that the second portion of the main body is greater than the first portion.

5. The arterial interluminal prosthesis of claim 1, further comprising wall stents in each of the first leg and the second leg, wherein the wall stents are substantially the same length as the corresponding legs.

6. The arterial interluminal prosthesis of claim 5, wherein the wall stents are longer than the corresponding legs.

7. The arterial interluminal prosthesis of claim 1, wherein the main body further includes two extensions at the second end for extending towards the iliac arteries.

8. The arterial interluminal prosthesis of claims 7, wherein the two extensions have first diameters and the first and second legs have second diameters larger than the first diameters to substantially seal the extensions.

9. The arterial interluminal prosthesis of claim 8, wherein the two extensions further include stents coupled within the extensions.

10. A method of inserting an arterial interluminal prosthesis into an aortic artery and iliac arteries of a patient, the method comprising the steps of:
    providing a main body having a first end with an aperture and a second end having two apertures;
    coupling a first stent to the first end of the main body such that a lower end of the stent is restricted in diameter and the opposing end is unrestricted in diameter;
    inserting the main body through a first iliac artery into the aortic artery such that the first end is located proximate to renal arteries of the patient and the first stent covers the renal arteries of the patient and the second end is located within the aortic artery and proximate the iliac arteries of the patient;
    providing a first leg separate from the main body;
    inserting the first leg through the first iliac artery into one of the two apertures of the main body to extend therefrom and into the first iliac artery;
    providing a second leg separate from the main body;
    inserting the second leg through a second iliac artery and into the other of the two apertures of the main body to extend therefrom into the second iliac artery.

11. The method of inserting an arterial interluminal prosthesis into an aortic artery and iliac arteries of a patient of claim 10, further comprising the steps of:
    providing wall stents in the first and second legs that are longer than the first and second legs;
    extending the wall stents into the main body beyond first ends of the first and second legs such that the wall stents hold the first and second legs to the main body;
    extending the wall stents beyond second ends of the first and second legs such that the wall stents hold the first and second legs to the first and second iliac arteries.

12. An arterial interluminal prosthesis for repairing an aortic aneurysm of a patient comprising:
    a main body being located within an aortic artery of a patient having a first end with an upper aperture for being located proximate to renal arteries of the patient and a second end having two lower apertures for being located in the aortic artery proximate iliac arteries of the patient;
    a first stent located entirely within the main body proximate the first end and a second stent coupled at the first end of the main body to extend therefrom across the renal arteries of the patient.

13. The arterial interluminal prosthesis of claim 12, further comprising at least one outer stent coupled to an outside surface of the main body proximate the second end of the main body such that the first sent supports a first portion of the main body exclusively from the inner surface of the main body and the outer stent supports a second portion of the main body exclusively from the outer surface of the main body.

14. The arterial interluminal prosthesis of claim 13, comprising a plurality of stents coupled to the outer surface of the main body, wherein at least one of such stents is located proximate the second end of the main body and the at least one other of such stents is coupled to the first stent such that the second portion that is supported exclusively from the outer surface of the main body is greater than the first portion.

15. The arterial interluminal prosthesis of claim 12, wherein the second stent is a Z-stent with a lower end that is restricted in diameter by the main body and an upper end that is unrestricted in diameter such that it can expand to secure the prosthesis to the aortic artery.

16. An arterial interluminal prosthesis for repairing an aortic aneurysm of a patient comprising:
    a main body having a first end with an upper aperture for being located proximate to renal arteries of the patient and a second end having two lower apertures for being located in the aortic artery proximate iliac arteries of the patient;

a first leg separate from the main body for inserting into one of the two lower apertures of the main body to extend therefrom into one of the iliac arteries;

a second leg separate from the main body for inserting into the other of the two lower apertures of the main body to extend therefrom into the other of the iliac arteries;

a first stent located entirely within the main body proximate the first end and a second stent coupled at the first end of the main body to extend therefrom across the renal arteries of the patient; and a plurality of stents coupled to the outer surface of the main body, wherein at least one of such stents is located proximate the second end of the main body and the at least one other of such stents is coupled to the first stent.

17. An arterial interluminal prosthesis for repairing an aortic aneurysm of a patient comprising:

a main body having a first end with an upper aperture for being located proximate to renal arteries of the patient and a second end having two lower apertures for being located in the aortic artery proximate iliac arteries of the patient;

a first leg separate from the main body for inserting into one of the two lower apertures of the main body to extend therefrom into one of the iliac arteries;

a second leg separate from the main body for inserting into the other of the two lower apertures of the main body to extend therefrom into the other of the iliac arteries; and a first stent located entirely within t he main body proximate the first end and a plurality of stents coupled to the outer surface of the main body, wherein at least one of such stents is located proximate the second end of the main body and the at least one other of such stents is coupled to the first stent.

* * * * *